United States Patent
Von Drasek et al.

(10) Patent No.: US 7,409,117 B2
(45) Date of Patent: Aug. 5, 2008

(54) DYNAMIC LASER POWER CONTROL FOR GAS SPECIES MONITORING

(75) Inventors: William A. Von Drasek, Oak Forest, IL (US); Shawn D. Wehe, Westford, MA (US); Mark G. Allen, Boston, MA (US)

(73) Assignees: American Air Liquide, Inc., Fremont, CA (US); Physical Sciences, Inc., Andover, MA (US)

( * ) Notice: Subject to any disclaimer, the term of this patent is extended or adjusted under 35 U.S.C. 154(b) by 258 days.

(21) Appl. No.: 11/045,513

(22) Filed: Jan. 31, 2005

(65) Prior Publication Data

US 2005/0225840 A1  Oct. 13, 2005

Related U.S. Application Data

(60) Provisional application No. 60/543,706, filed on Feb. 11, 2004.

(51) Int. Cl.
   *G01N 21/35* (2006.01)
(52) U.S. Cl. .......................................... 385/12; 356/437
(58) Field of Classification Search ......... 356/300–334, 356/432–442, 246; 359/333; 250/336.1–395; 385/12
   See application file for complete search history.

(56) References Cited

U.S. PATENT DOCUMENTS

| | | | |
|---|---|---|---|
| 5,134,276 A | | 7/1992 | Hobbs |
| 5,185,643 A | * | 2/1993 | Vry et al. ..................... 356/506 |
| 5,252,060 A | * | 10/1993 | McKinnon et al. ............ 431/12 |
| 5,252,834 A | * | 10/1993 | Lin .......................... 250/458.1 |
| 5,293,213 A | * | 3/1994 | Klein et al. .................. 356/484 |
| 5,301,014 A | * | 4/1994 | Koch .......................... 356/437 |
| 5,448,071 A | * | 9/1995 | McCaul et al. .............. 250/343 |
| 5,636,035 A | * | 6/1997 | Whittaker et al. ........... 356/437 |
| 5,748,325 A | * | 5/1998 | Tulip .......................... 356/437 |
| 5,813,767 A | * | 9/1998 | Calabro' et al. ............. 374/142 |
| 6,069,697 A | * | 5/2000 | Tanimoto et al. ............ 356/327 |
| 6,252,689 B1 | * | 6/2001 | Sharp ......................... 398/168 |
| 7,157,712 B2 | * | 1/2007 | Flanders et al. ........ 250/339.07 |

(Continued)

OTHER PUBLICATIONS

Richter, Dirk, Lancaster, David, G., and Tittel, Frank, K., Development of an Automated Diode-laser-based Multicomponent Gas Sensor, Applied Optics, vol. 39, No. 24, Aug. 2000.

(Continued)

*Primary Examiner*—Deandra M. Hughes
*Assistant Examiner*—Ari M Diacou
(74) *Attorney, Agent, or Firm*—Elwood L. Haynes

(57) ABSTRACT

A gas species monitoring system includes a laser, a fiber amplifier configured to receive an input signal from the laser and generate an amplified signal, and a variable optical attenuation system configured to receive at least a portion of the amplified signal and generate an attenuated signal for delivery to a measurement point, where the measurement point includes a gaseous fluid. The system further includes a detector configured to receive and process a signal from the measurement point so as to obtain a measured signal that correlates with the presence of a gas species within the gaseous fluid at the measurement point, and a processor in communication with at least the variable optical attenuation system and the detector. The processor controls the variable optical attenuation system based upon the measured signal.

12 Claims, 8 Drawing Sheets

U.S. PATENT DOCUMENTS

| | | | |
|---|---|---|---|
| 7,244,936 B2* | 7/2007 | Von Drasek | 250/339.13 |
| 7,248,755 B2* | 7/2007 | Sappey et al. | 385/13 |
| 7,274,028 B2* | 9/2007 | Fishkin et al. | 250/459.1 |
| 2002/0031737 A1 | 3/2002 | Von Drasek et al. | |
| 2002/0185240 A1* | 12/2002 | Drake, Jr. | 162/198 |
| 2003/0132389 A1* | 7/2003 | Von Drasek et al. | 250/343 |
| 2003/0152307 A1 | 8/2003 | Von Drasek et al. | |
| 2003/0160174 A1 | 8/2003 | Grant et al. | |
| 2003/0218752 A1 | 11/2003 | Von Drasek et al. | |
| 2005/0254056 A1* | 11/2005 | Kachanov et al. | 356/437 |
| 2006/0065834 A1* | 3/2006 | Flanders et al. | 250/339.07 |
| 2006/0133714 A1* | 6/2006 | Sappey et al. | 385/13 |

OTHER PUBLICATIONS

Ray, G. J., Anderson, T. N., Lucht, R. P., Walther, T., and Caton, J. A., Fiber-Amplified, Diode-Laser-Based Sensor for OH Absorption, Paper No. 268, Second Joint Meeting of the U.S. Sections of the Combustion Institute, Oakland, CA, Mar. 25-28, 2001.

Weber, Micheal, E., Pushkarsky, Michael, B., and Patel, Kumar, N., Ultra-Sensitive Gas Detection Using Diode Lasers and Resonant Photoacoustic Spectroscopy, SPIE's International Symposium and Technology, Diode Lasers and Applications, Paper No. 4871-11, Jul. 2002.

Sonnenfroh, D., Sewell, S., and Allen, M., "An Ultrasensitive Detection Techniques for Tunable Diode laser Spectrometers: Application to Detection of $NO_2$ and $H_2O$", Proceedings of the Society of Photo-optical Instrumentation Engineers, vol. 2834, pp. 60-66, 1996.

W. Von Drasek, K. Mulderink, S. Wehe, and M. Allen Multiple Gas Species Detection using a Tunable Diode Laser Sensor for Combustion Process Monitoring American Institute of Chemical Engineers 2002 Annual Meeting, Sensors for Process Control and for the Chemical Industry I, Indianapolis, IN, Nov. 3-8, 2002.

Dietrich, A., Kaspersen, P., and Sommerauer, H., "Laser Analysis of CO and Oxygen in EAF Off-Gas", $59^{th}$ Electric Furnace Conference and $19^{th}$ Process Technology Conference Proceedings, Iron and Steel Society, 2001.

Von Drasek, W.; "Tunable Diode Laser Sensor for Monitoring and Control of Harsh Combustion Environments"; Quarterly Progress Report No. 15 (DE-FC36-00CH11030), Chicago Research Center, Jan. 30, 2004; 29 pages.

* cited by examiner

DYNAMIC LASER POWER CONTROL FOR GAS SPECIES MONITORING

CROSS-REFERENCE TO RELATED APPLICATIONS

This application claims priority from U.S. Provisional Patent Application Ser. No. 60/543,706, entitled "Dynamic Laser Power Control For Harsh Processes and Distributed Gas Monitoring", and filed Feb. 11, 2004. The disclosure of this provisional patent application is incorporated herein by reference in its entirety.

BACKGROUND OF INVENTION

1. Field of Invention

The present invention pertains to controlling laser power for effectively identifying and monitoring concentrations of the constituents or species within a gas stream under harsh and/or other processing conditions.

2. Related Art

Optical fiber amplifier technology has historically focused on communication applications. The use of optical amplifiers in this technology allows a communication signal to remain in the optical domain of the transmission link without changing back to the electrical domain as experienced by opto-electronic signal regenerators. In the early signal transmissions systems, optical signal attenuation resulting from losses in the fiber was recovered by a repeater, which converts the optical signal into an electrical signal that can be reshaped, retimed, and regenerated back to an optical signal for continued transmission. The drawback of the electronic regenerative repeaters is the need for high-speed electronics that becomes increasingly complex and problematic in terms of equipment size and bit rate transmission. These problems were overcome by implementing an active fiber amplifier that reshapes the transmission signal completely in the optical domain.

Optical fiber amplifier technology is well known in the art, and the theory of operation, characteristics, and applications of this technology has been described in *Sudo Shoichi, Optical Fiber Amplifiers: Materials, Devices, and Applications, Artech House, Inc.*, 1997. Briefly, the operating principle of the fiber amplifier is based on using a rare-earth doped section of fiber to amplify the entering optical signal using stimulated emission of the optically excited rare earth ions in the fiber core that are pumped by a semiconductor laser. The amplified signal exiting the fiber can be several orders of magnitude higher than the input signal with minimal addition of intensity noise (typically less than 7 dB). A summary of all the rare-earth ion energy levels and laser transitions that have been reported and that span a wavelength range from 0.172-5.15 µm is described in Caird, J. A. and Payne, S. A., *Crystal Paramagnetic Ion Lasers, CRC Handbook of Laser Science and Technology, Supplement 1: Lasers*, Weber, M. J., (ed.), Boca Raton Fla.: CRC Press, pp 3-100, 1991. The transitions lying between 0.8 µm and 1.6 µm are of particular importance in applications where fiber optic lines exhibit low losses (e.g., telecommunication applications). In this region, the rare earth dopant fiber amplifiers such as erbium-doped fiber amplifier (EDFA), praseodymium-doped fiber amplifier (PDFA), thulium-doped fiber amplifier (TDFA), neodymium-doped fiber amplifier (NDFA), and ytterbium-doped fiber amplifier (YDFA) are used. The amplification bands and bandwidth are dependent on the different kinds of dopants used in the fiber composition. The form of the bandwidth can also be influenced by utilizing co-dopants and host glass material. Of the different rare earth dopant amplifiers, EDFA's have received the greatest attention due to the low fiber attenuation loses in the C (1530 nm-1565 nm) and L (1565 nm-1605 nm) bands that are used for telecommunication applications.

An energy diagram for fiber amplification is depicted in FIG. 1 based upon the selection of the rare-earth element erbium and 1.5 µm light amplification. In the 1.5 µm region, a 980 nm pump laser can be used to pump the $^4I_{11/2}$ level. Population of the $^4I_{13/2}$ level occurs via fast nonradiative decay with vibrational phonons of the crystal lattice. Subsequently, signal photons near 1.5 µm are multiplied through stimulated emission from the $^4I_{13/2}$ level to the ground state. While it is noted that the pump laser choice is not restricted to 980 nm, an EDFA based on a 980 nm pump laser has favorable noise characteristics. There are multiple choices for the pump laser, but for practical EDFA's, 980 nm and 1480 nm pumping are mainly used due to their pump efficiency and high-output power characteristics.

For commercially available fiber amplifiers (FA), three standard modes of operation are used: automatic power control (APC), automatic gain control (AGC) and automatic current control (ACC). APC mode takes a calibrated power reading from an optical tap on the output. This measured value is used as feedback for a control loop which adjusts the pump-laser injection current to keep the output power constant. AGC mode is similar except taps are located in the input and output portions of the amplifier and the injection current is automatically adjusted to maintain a fixed ratio. ACC mode includes two types of control loops, the first type of control loop monitors the pump laser output power and adjusts the injection current to keep pump power constant, while the second type of control loop monitors and controls the injection current independent of the output power.

In addition to telecommunication applications, fiber amplifiers are also utilized in systems for facilitating spectroscopy measurements of molecules, where the amplifier is used for nonlinear wavelength mixing applications and photoacoustic spectroscopy. Application of near-IR laser systems for in-situ process monitoring relies on the ability to transmit a laser beam or signal through the process and receive sufficient radiation at the detection side for monitoring gas species concentration and/or gas temperature. On processes with high particle densities, the transmission of light can be severally affected requiring a measurement pathlength reduction and/or increasing the laser power. However, available diode lasers used in the near-IR region have limited power output. Overcoming the power limitation can be obtained using a fiber amplifier to extend the power range of the laser by several orders of magnitude for improved transmission and background discrimination.

For example, it is known to implement a Yb fiber amplifier to generate 600 mW at 1083 nm from an input laser power of about 15 mW for difference frequency mixing (DFM) to produce tunable radiation in the mid-IR range between 3-5 µm. See, e.g., Richter, Dirk, Lancaster, David, G., and Tittel, Frank, K., *Development of an Automated Diode-laser-based Multicomponent Gas Sensor, Applied Optics*, Vol. 39, No. 24, August 2000 and Lancaster, D. G., Richter, D., and Tittel, F. K., *Portable Fiber-coupled Diode-laser-based Sensor for Multiple Trace Gas Detection, Applied Physics B, Vol. 69*, 1999. In these applications, two near-IR diode lasers are mixed in a nonlinear optical material such as periodic poled lithium niobate (PPLN) to generate narrow linewidth tunable mid-IR radiation. Access to the mid-IR radiation range has applications for trace gas sensing constituents or species such as $CO_2$, $NO_2$, $CH_4$, $N_2O$, HCl, $H_2CO$, $CH_3OH$, and $C_6H_6$. Implementing a fiber amplifier into the optical layout is beneficial since the resulting output power levels generated from DFM are dependent on the input power used with the nonlinear optical material. Thus, the use of µW power levels in the mid-IR range are possible in these systems by utilizing the increased power boost provided by the Yb fiber amplifier.

As described in Ray, G. J., Anderson, T. N., Lucht, R. P., Walther, T., and Caton, J. A., *Fiber-Amplified, Diode-Laser-Based Sensor for OH Absorption*, Paper No. 268, Second Joint Meeting of the U.S. Sections of the Combustion Institute, Oakland, Calif., Mar. 25-28, 2001, an Nd-doped fiber amplifier is used for second harmonic generation of 532 nm light from a PPLN crystal that was further frequency doubled with BBO (beta barium borate) to generate 266 nm for OH absorption measurements in a hydrogen-air flame. Here, an ECDL (external cavity diode laser) was utilized to produce 20 mW of the fundamental 1064 nm that was amplified to 1 W using a NDFA. As in the previously described DFM system, higher input laser power for these nonlinear mixing processes produces higher output powers that are useable for practical measurement systems. An advantage for using a fiber amplifier with the nonlinear mixing techniques such as DFM and SHG is an instrumentation size reduction and reduced complexity by using standard diode lasers and fiber optic components.

It is known to utilize a fiber amplifier in a laser powered gas monitoring system to facilitate the direct measurement of a chemical species, as described in Weber, Micheal, E., Pushkarsky, Michael, B., and Patel, Kumar, N., *Ultra-Sensitive Gas Detecion Using Diode Lasers and Resonant Photoacoustic Spectroscopy, SPIE's International Symposium and Technology, Diode Lasers and Applications*, Paper Number 4871-11, July 2002. In this system, an EDFA is used for $CO_2$ and $NH_3$ detection by photoacoustic spectroscopy. This system employs a technique where a laser beam passes through a sample cell containing a gas species having an absorption transition within the tuning range of the laser. As the laser wavelength is tuned to an absorption transition of the molecule the upper energy level is populated. By collision with other atoms or molecules in the cell, these excited molecules transfer their excitation energy completely or partly with collision partners. This energy transfer process results in a rise of temperature and pressure at a constant density in the sample cell. By sweeping the laser wavelength periodically across the molecule absorption transition, periodic pressure variations in the cell emerge, and these pressure variations can be detected with a sensitive microphone. The resulting signal strength observed is directly proportional to the incident laser power.

In U.S. Pat. No. 6,252,689, a distributed fiber network system is described for conducting measurements at multiple locations of an external condition, such as humidity, temperature, gas, pressure, object location, people detection, air velocity, and displacement. Here, the use of a fiber amplifier incorporated into the distributed fiber network is used to boost laser power that has been attenuated by the number of switches, hubs, open path cells, etc., and to act as a repeater for boosting returning optical signals that have undergone attenuation. For this monitoring concept, both bidirectional and unidirectional operation is proposed with the light signal affected by the specific measurement (external condition) returned by fiber optic to the centralized detection system. Insertion losses for each of these components in the network can influence the measurement capability. This system is designed for ambient monitoring and uses a centralized light source, laser or LED, and detection system with the light distributed to multiple locations through a network of switches and hubs. However, the '689 patent does not disclose utilizing the fiber amplifier for transmission improvements due to loses by particulate matter or controlling the laser power at different measurement locations.

The use of a fiber amplifier in a system for directly monitoring gas species is described in U.S. Patent Application Publication No. 2003/0132389, the disclosure of which is incorporated herein by reference in its entirety. In this system, several variations are presented for using a diode laser with a fiber amplifier. In the embodiments described in this reference, the control of the laser power delivered to a particular process was performed by adjusting the pump laser power to thereby adjust the amplifier gain.

In applications where control of the laser power over a large dynamic range is required, or when a portion of the laser radiation is used for a reference, the nonlinear behavior of the fiber amplifier can be problematic in carrying out the measurement. In addition to the non-linearity of the FA, other aspects of the FA operating characteristics, such as noise added to the output radiation, are important considerations that place limitations on the gas sensing detection limits. For example, the noise figure (NF) given by the following equation:

$$NF = 10 \log \frac{(S/N)_{IN}}{(S/N)_{OUT}} \quad (1)$$

where S is the signal and N is the noise, a theoretically best obtainable value is 3 dB, with typical devices performing no better than 4.5 dB. Saitoh, T. and Mukai, T, "1.5 mm *GAIN-ASP Teaveling—Wave Semiconductor Laser Amplifier*, *IEEE Journal of Quantum Electronics*, vol. 23, no. 6, June 1987.

The NF data from the *CATV Amplifier User's Manual* (provided by Keopsys, Inc. of Hampton, N.J.) for an EDFA is depicted in FIG. 2 as a function of input power for a range of gain settings and when operating at a fixed wavelength of 1560 nm. This figure illustrates the variation for NF at different gain levels, with gain being defined by the following equation:

$$G = 10 \log \left( \frac{P_{out}}{P_{in}} \right) \quad (2)$$

where $P_{in}$ is typically referenced at 1 mW laser input laser power yielding units of dBm on the gain. FIG. 2 indicates that, for various gain settings, the resulting NF ranges from below 5 dB to greater than 8 dB. The higher NF values occur at low gain conditions, e.g., conditions with input powers near 10 dbm (10 mW) and output power of 13 dbm (20 mW). Therefore, operating at higher gain is preferred to minimize the NF on the output. Dynamic process monitoring where the gain must be varied due to changes in the transmission will result in poorer signal detection when the gain must be reduced to lower levels to avoid detector saturation. The added noise resulting from the gain change will in turn reduce the measurement quality.

Output power versus input power data at different wavelengths residing in the C-band for the EDFA is depicted in FIG. 3. In particular, FIG. 3 illustrates two main effects on the operation of the EDFA. First, at low input powers the gain is a strong function of the wavelength that can influence the measurement for multiplexed laser systems that span a large wavelength region. For example, when operating the EDFA with a sampled grating-DBR laser that is capable of tuning over the 40 nm C-band wavelength range, or with a multiplexed laser system using several DFB lasers and beam combiners, would result in variations in the output power at different wavelengths. If the application requires monitoring both 1540 nm and 1560 nm wavelengths with a low input power of −6 dBm (0.25 mW), the variation in the output power between the two wavelengths would be 94 mW, which would saturate the detection electronics when monitoring the 1540 nm radiation.

Second, for a fixed wavelength the performance of the amplifier is nonlinear, where linearity is expressed as operation with constant gain. The dashed curve in FIG. 3 illustrates the expected linear performance behavior if achievable at 1560 nm for a constant gain of 20 dBm. Linear performance of such amplifiers is only achieved over a small input range of about −22 dBm to about −18 dbm (6.3 µW-16 µW). At these low input levels, the advantages of using an amplifier are lost, since the resulting output laser powers are between 3 to 8 mW (assuming 27 dBm gain, i.e., 500× amplification for the linear range input powers). Laser powers in this range and greater are easily achieved from standard off-the-shelf telecommunication DFB diode lasers without amplification.

SUMMARY OF THE INVENTION

It is an object of the present invention to provide a laser power control system for detecting gas species that is capable of operating over a selected range of output laser powers while maintaining accuracy and reliability in detecting the presence and concentration of constituents or species in a gas stream.

It is another object of the present invention to provide a laser power control system for detecting gas species that is operable in dynamic and steady state modes.

It is a further object of the present invention to provide a laser power control system for detecting gas species that can be utilized for monitoring a plurality of measurement points with varying process conditions.

The aforesaid objects are achieved individually and/or in combination, and it is not intended that the present invention be construed as requiring two or more of the objects to be combined unless expressly required by the claims attached hereto.

In accordance with an embodiment of the present invention, a gas species monitoring system includes a laser, a fiber amplifier configured to receive an input signal from the laser and generate an amplified signal, and a variable optical attenuation system configured to receive at least a portion of the amplified signal and generate an attenuated signal for delivery to a measurement point, where the measurement point includes a gaseous fluid. The system further includes a detector configured to receive and process a signal from the measurement point so as to obtain a measured signal that correlates with the presence of a gas species within the gaseous fluid at the measurement point, and a processor in communication with at least the variable optical attenuation system and the detector. The processor controls the variable optical attenuation system based upon at least the measured signal.

In accordance with another embodiment of the present invention, a gas species monitoring system includes a laser, a fiber amplifier configured to receive an input signal from the laser and generate an amplified signal at a greater power level than the input signal, and a variable optical attenuation system configured to receive and process the amplified signal so as to obtain an attenuated signal at a selected power level. The system also includes a gas species detection zone including at least one circuit, where the circuit includes a launch module configured to receive the attenuated signal from the variable optical attenuation system and collimate the signal for delivery to a measurement point, the measurement point including a gaseous fluid, and a receiver module to receive the signal emerging from the measurement point, the receiver module including a detector configured to process the signal from the measurement point so as to obtain a measured signal that correlates with the presence of at least one gas species within the gaseous fluid. The system further includes a processor in communication with at least the detector of the receiver module and the variable optical attenuation system, where the processor receives information regarding the measured signal and selectively controls the variable optical attenuation system based upon the measured signal.

Optionally, a reference system (e.g., a balance ratiometric detector) is further provided, and the amplified signal is split by a splitter, with one split signal being directed to the reference system and another split signal being directed to the variable optical attenuation system. The processor then selectively controls the variable optical attenuation system based upon a comparison of a reference signal obtained from the reference system and a measured signal obtained from the detector of the receiver module.

The combination of fiber amplifier (FA) and a variable optical attenuation system into a gas species monitoring system in accordance with the present invention renders the system operable in both a dynamic or steady state mode. In addition, using the FA/VOA combination with beam splitters and/or optical switches extends the range of multiplexed measurement applications that can be implemented utilizing this system. With this configuration, a plant-wide distributed measurement system can be performed using a single diode laser that is adaptable to measurement points with varying process conditions, e.g., transmission characteristics.

The above and still further objects, features and advantages of the present invention will become apparent upon consideration of the following detailed description of specific embodiments thereof, particularly when taken in conjunction with the accompanying drawing.

DESCRIPTION OF PREFERRED EMBODIMENTS

In accordance with the present invention, a gas species monitoring system employing a laser combined with a fiber amplifier (FA), e.g., an erbium doped fiber amplifier (EDFA), and a variable optical attenuation system provides linear control for the output laser power being sent to the measurement point or points as well as a high level of accuracy in the gas species detection and concentration measurements over a range of wavelengths and output laser power values for the FA. In particular, the system is suitable for gas species monitoring applications where attenuation or background noise (radiation) are problematic.

Figure 1:
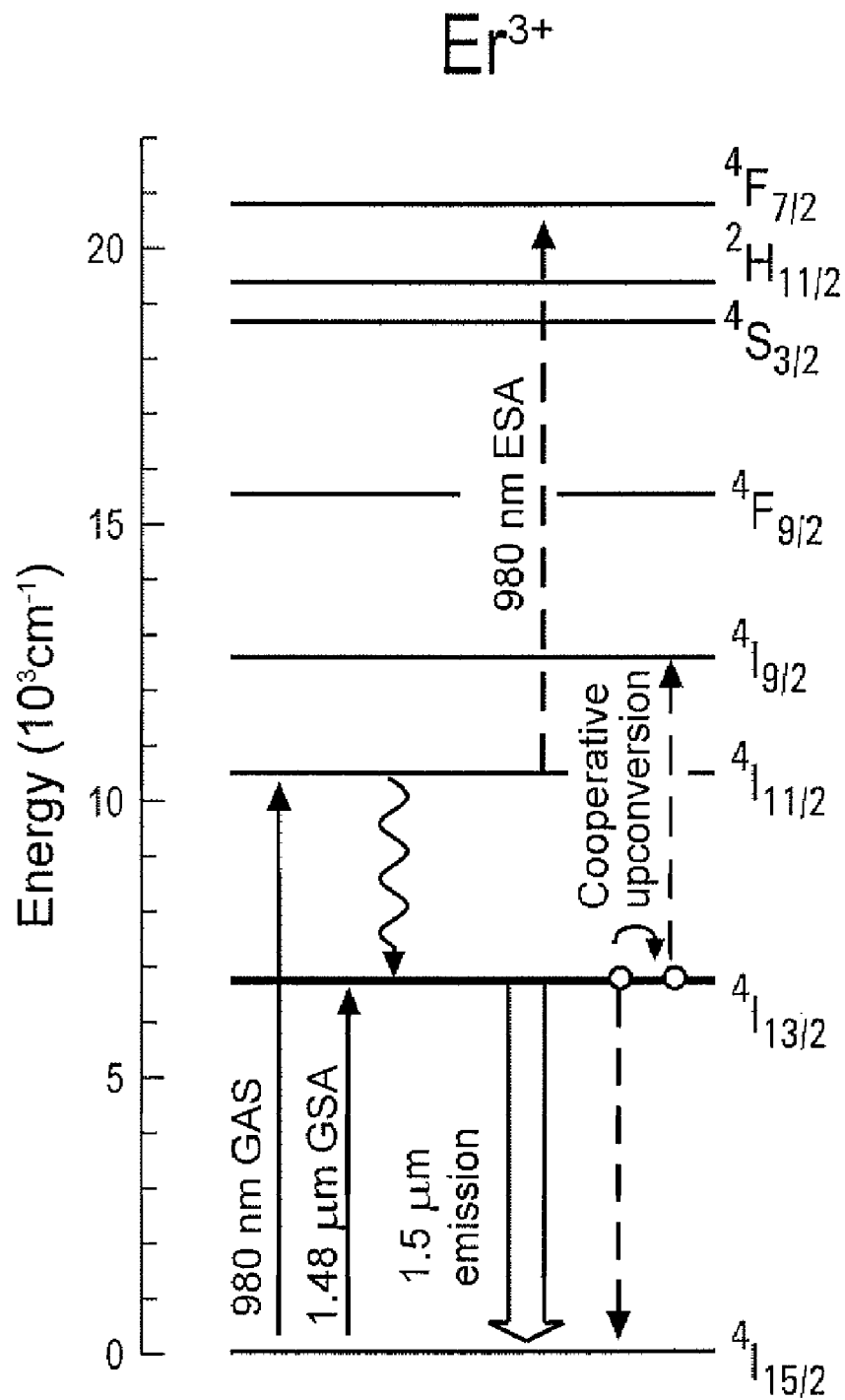
FIG. 1 is an erbium-doped energy diagram for fiber amplification.
Figure 2:
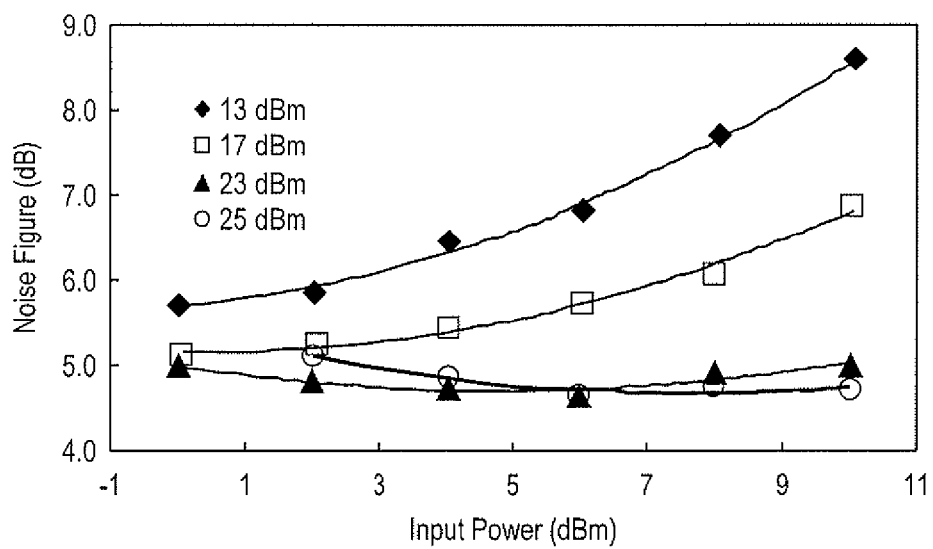
FIG. 2 is a plot of Noise Figure vs. input laser power over a range of gain settings.
Figure 3:
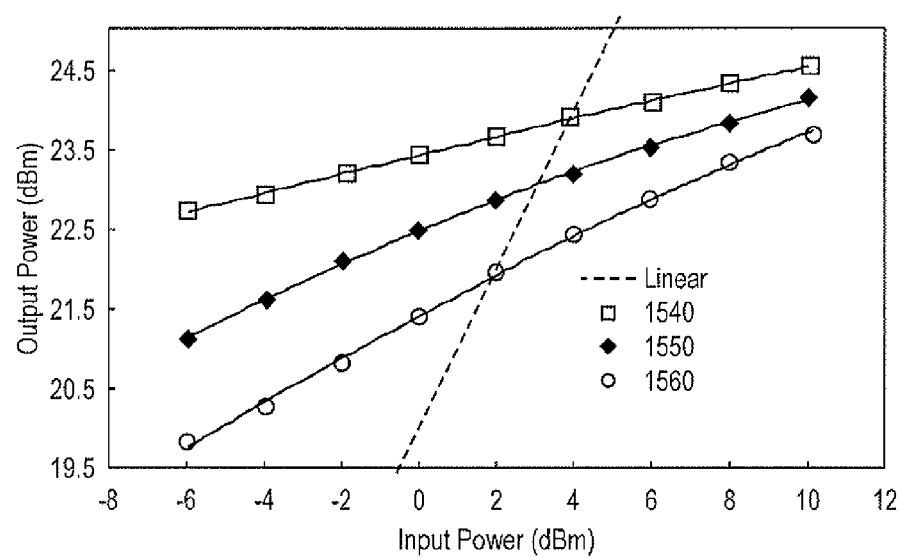
FIG. 3 is a plot showing the nonlinearity of output power or gain as a function of input power over a range of wavelengths.
Figure 4:
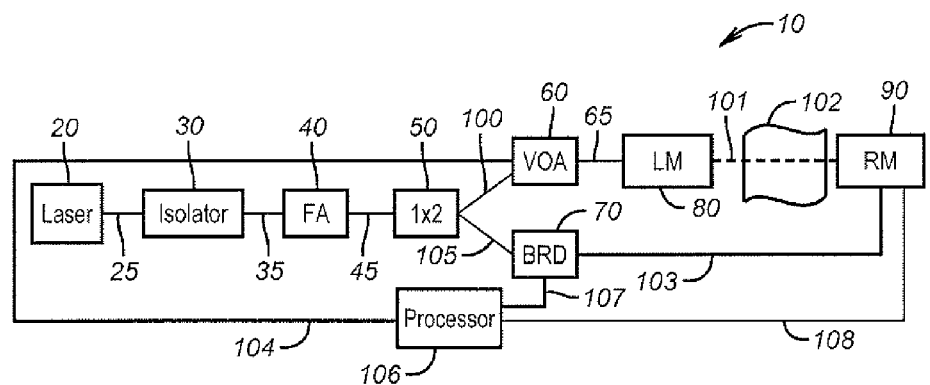
FIG. 4 depicts an exemplary embodiment of a gas species monitoring system utilizing a combination of a fiber amplifier (FA) and variable optical attenuator (VOA) in accordance with the present invention.

An exemplary embodiment of a system that combines a semiconductor laser device with a fiber amplifier (FA) and a variable optical attenuator (VOA) in a gas species monitoring system is depicted in FIG. 4. System 10 includes a diode laser 20 that is tunable over an absorption transition of a selected gas species.

Exemplary gas species that are monitored in the system include, without limitation, $O_2$, $H_2O$, $H_2$, $CO$, $CO_2$, $NO_2$, $OH$, $N_2O$, $HCl$, $H_2CO$, alkyl species (e.g., $CH_4$) and various other pollutants such as $SO_x$. Exemplary diode lasers suitable for use in the systems of the present invention include, without limitation, InGaAs/InP diode lasers lasers such as the type available from NTT Electronics Corporation (Tokyo, Japan). The laser 20 delivers a laser signal via a fiber optic line 25 and at a selected input laser power value to a FA 40. It is further noted that fiber optic lines are utilized to connect many of the system components to facilitate transfer of the laser radiation or signal between the components during system operation. An exemplary FA suitable for use in system 10 is a single stage OEM 24 dbm EDFA available from Keopsys, Inc. (Hampton, N.J.). Optionally, an isolator 30 is situated in-line between the laser 20 and FA 40, with optical lines 25 and 35 connecting the components to each other, to protect the laser from amplified reflections that could damage the laser.

A 1×2 fiber splitter 50 is disposed within system 10 to receive the amplified laser signal from FA 50, via an fiber optic line 45, and to divide the laser signal into two separate fiber optic line legs or lines, where the first line 100 extends to a VOA 60 and the second line 105 extends to a reference cell or system. The reference system depicted in FIG. 4 is a balance ratiometric detector (BRD) 70. An exemplary BRD circuit that is suitable for use in the system of the present invention is the BRD described in U.S. Pat. No. 5,134,276, the disclosure of which is incorporated herein by reference in its entirety. However, it is noted that the reference system can be any suitable device that is effective in laser line locking and, optionally, calibrating the signal. The 1×2 splitter can split the power of the laser signal into any suitable fractions between the resultant two signals. An exemplary laser power division by the 1×2 splitter is to divide the laser power such that about 30% is directed through the first line 100 to the VOA 60, while about 70% is directed through the second line 105 to the BRD 70. The VOA 60 attenuates and ultimately directs the split laser signal to a selected measurement point (MP) 102.

Selection of a suitable variable optical attenuation system for a particular application will be based on system performance requirements. For example, a single variable optical attenuator (VOA) can be used, such in the configuration of system 10 depicted in FIG. 4. Exemplary VOA's suitable for use in the present invention include, without limitation, the EXFO 3100 series of VOA's (EXFO Corporation, Quebec, Canada) that have an operability based on a wedged gradient filter that intercepts the light. The wedged filter can move in and out thereby varying the level of attenuation. Other variable optical attenuation systems that are suitable for use in the present invention include devices based on MEM (micro electronic manufacturing) technology, such as VOA devices available from DiCon Fiberoptics, Inc. (Richmond, Calif.). The operability of a MEMS attenuator is based on a mirror rotation that changes the coupling of light between the input and output. In addition, another variable optical attenuation system could include a series of fixed optical attenuators that are independently and separately connected to a suitable splitter or optical switch. Thus, the term "variable optical attenuation system", as used herein and in the claims, refers to any system that is selectively controlled and is capable of varying attenuation of an output laser signal from a FA prior to delivery to a selected measurement point (MP). The choice of a specific variable optical attenuation system for a particular scenario will be dependent on factors such as the time response required to vary the light level, the level of attenuation required, and the acceptable noise level the component can add to the optical system.

The variable optical attenuation system of the present invention can be used as a single VOA unit (as depicted in FIG. 4) or as a cascade of several units (e.g., as in the systems described below and depicted in FIGS. 6 and 7). The addition of a suitable variable optical attenuation system eliminates the necessity for linearity and gain control of the amplifier. In other words, with this configuration, the amplifier can operate at a fixed gain while the power available to the measurement point (MP) 102 is adjusted by the variable optical attenuation system.

A launch module (LM) 80 is provided within the system to receive the attenuated laser signal from the VOA 60, via fiber optic line 65, and includes suitable shaping and collimating optics to collimate the laser beam or signal to a selected diameter and divergence before sending the signal to the MP 102. From the LM 80, laser radiation is propagated through the MP 102 (as indicated by dashed line 101 in FIG. 4) and is then collected at a receiver module (RM) 90 that includes mirrors and/or other suitable optics as well as at least one photodetector to monitor the intensity of the laser beam or signal that is received from the measurement point (MP) 102 so as to correlate the intensity with the presence and concentration of gas species within the MP 102. The selection of a suitable photodector for the RM will depend upon the particular application. Exemplary photodectors for use in the present invention include, without limitation, silicon photodetectors available from EG&G Optoelectronics (Gaithersburg, Md.) and InGaAs detectors available from Fermionics (Simi Valley, Calif.). The launch and receiver modules can be of any conventional or other suitable type including, without limitation, those that are described in U.S. Patent Application Publication No. 2003/0152307, the disclosure of which is incorporated herein by reference in its entirety.

The measurement point (MP) can be disposed at any suitable location within a gas-flow system to facilitate an in-situ process analysis and measurement of a gas flowing through the system at the MP. For example, the MP can be situated within a particular system to measure any of the following: an off-gas in the furnace exhaust duct of an electric arc furnace (EAF) system, a gas near or in the primary combustion chamber of a waste incinerator exhaust duct, a gas at any selected monitoring location in a coal-fired boiler or recovery boiler, the off-gas from a secondary aluminum rotary or reverberatory furnace, the gas of a basic oxygen furnace (BOF), blast furnace gases, etc., where the measurement can be enhanced by increasing and/or controlling the laser power.

Alternatively, the MP could also consist of an ex-situ system, where the MP consists of a sample cell or external measurement zone that receives an extracted process gas from a selected location within the system for analysis and measurement of gas species. An example of such an ex-situ MP is described in U.S. Patent Application Publication No. 2003/0160174, the disclosure of which is incorporated herein by reference in its entirety. The standard diode laser monitoring system described in this published reference can be modified, in accordance with the present invention, so as to further include the combination of an FA and VOA. The additional laser power that is available by modifying the system in this manner improves the measurement accuracy of gas species with reduced process gas filtering and/or enables the addition of a multiple pass cell configuration for improving the signal-to-noise ratio (SNR) during system operation. In addition, the system of the present invention can include a MP location having an open path measurement zone without significant loss in detection and concentration measurement accuracy. This is in contrast to conventional laser power gas species monitoring systems employing such MP configurations and encounter problems such as laser power losses due to attenuation by particulate matter and/or fog.

The laser power monitored by the receiver module (RM) 90 can be correlated to species detection and concentration in any suitable manner. For example, gas species detection and concentration within the RM can be determined by application of Beer's law in a manner similar to that described in U.S. Patent Application Publication No. 2002/0031737, the disclosure of which is incorporated herein by reference in its entirety. Any suitable processor can be provided at any suitable location within the system to determine the concentration of one or more gas species at the measurement point (MP) based upon the laser power monitored by the receiver module and/or the reference signal processed by the BRD (or other suitable reference system).

Referring to FIG. 4, a signal (sig) processed by RM 90 is sent, via fiber optic line 103, to BRD 70. The BRD 70 also receives a reference signal (ref) from 1×2 splitter 50 (via the second line 105). In this configuration, the BRD suppresses common mode laser noise by 5 orders of magnitude or 50 dB. Sonnenfroh, D., Sewell, S., and Allen, M., "*An Ultrasensitive Detection Techniques for Tunable Diode laser Spectrometers: Application to Detection of $NO_2$ and $H_2O$*", Proceedings of the Society of Photo-optical Instrumentation Engineers, Vol. 2834, pp. 57-66, 1996.

The BRD allows monitoring of the true absorption lineshape to extract the species concentration by a simple scan-and-integrate approach. True line shape monitoring provides an absolute concentration measurement that is immune to temperature and broadening mechanisms. In addition, by scanning the laser over the full lineshape, including the baseline, reduces the effect of broadband absorbers and emitters.

The temporal response of the BRD is optimal when the ratio of the signal (input via line 103) and reference (input via line 105), represented as the ref/sig ratio, is near a value of 2. In systems where the measurement region is well controlled, the 1×2 beam splitter typically divides the laser power with 70% to the reference channel (i.e., line 105 in FIG. 4) and 30% to the signal channel (i.e., line 10 in FIG. 4). However, for industrial process-monitoring applications, maintaining the ref/sig ratio near 2 can be difficult due to losses from process particulate matter, since the ref/sig ratio is a measure of the transmission through the measurement volume. System 10 compensates for this with a processor 106. The processor 106 receives and processes signals from BRD 70, via communication link 107 (e.g., electrical wiring and/or wireless communication links). The processor compares the signals to determine the observed deviation in the ref/sig ratio value. The ref/sig ratio value can be adjusted as necessary by feedback control provided by processor 106 to the VOA 60 via a feedback communication link 104.

In addition, the processor can also be configured to utilize the processed signals received from the BRD and/or the RM to identify and determine concentrations of gas species at the measurement point. Referring to FIG. 4, a communication link 108 is provided between processor 106 and the detector of RM 90 to facilitate the direct transfer of information relating to the measured signal by the detector to the processor. In addition, while the embodiment of FIG. 4 employs the use of a reference signal in addition to the measured signal at the RM detector to determine how to adjust the VOA, it is noted that adjustment of the VOA and/or determination of gas species concentrations can be achieved by analysis of only the signal as measured by the RM detector.

Referring again to the embodiment of FIG. 4, the VOA setting is selectively adjusted by the processor based on the observed ref/sig ratio as determined by the BRD and/or the processor. In a preferred method, the amplifier operates at saturated gain (constant output power) with adjustment of the VOA providing the necessary linear power control of the laser. For monitoring applications where the ratio varies within a well-defined window or range, direct use of the signal from the receiver detector in RM 90 can be used. For example, in any process where the variation in the transmission through the measurement volume in MP 102 varies continuously, smoothly, and slowly, feedback control based on the signal form the receiver detector can be used.

Figure 5:
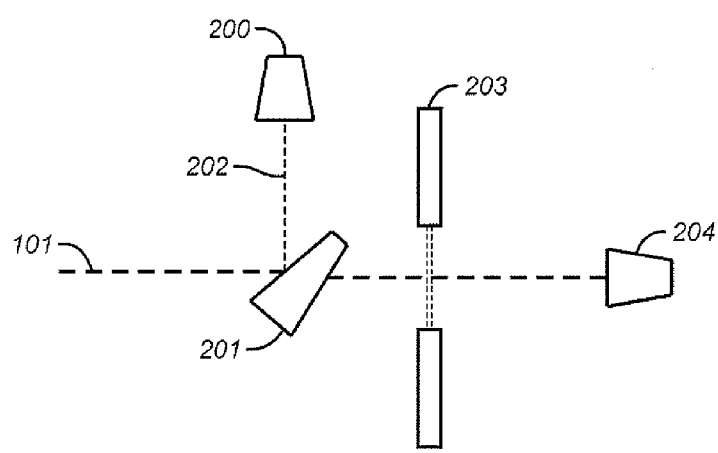
FIG. 5 depicts an exemplary embodiment of a configuration of optics and other components for the receiver module of the system of FIG. 4.

If however, the process dynamics vary rapidly (e.g., the particle loading variation affects the transmission on a short time scale), such that the receiver detector may be exposed to high laser power due to the slow response of the VOA, use of a secondary monitoring system in the receiver module (RM) is preferable. When highly dynamic process monitoring is required, the RM is configured to include a number of detectors. An exemplary embodiment of such a RM is depicted in FIG. 5. In particular, the RM includes a wedge optic 201 that partially deflects laser beam signal 101 as the signal enters the RM. The partially deflected signal (depicted as dashed line 202) is directed to a first photodetector 200. The main portion (>90%) of laser signal 101 is directed to a second photodetector 204, and photodetector 204 in turn sends the signal to the BRD. A comparator circuit is used to compare the output from photodetector 200 with a set-point value. The signal from detector 200 is sent to the processor 106 (as shown in FIG. 4) for use in controlling the setting of VOA 60. A shutter 203 that is selectively and automatically manipulated is also provided at a location between optic 201 and photodetector 204. If the laser power monitored by photodetector 200 exceeds the set-point value, then shutter 203 is manipulated to a closed position to protect photodetector 204 from receiving the high power laser radiation that would otherwise damage the photodetector. When the laser power decreases to an acceptable level, either by adjusting the VOA or by changing transmission through the process, shutter 203 will then be manipulated to an open position. In this mode of operation, periods with no process monitoring can occur during an adjustment period of the VOA.

The success of a control strategy utilizing the RM of FIG. 5 can be measured as the fraction of time that useable measurement data is obtained and will be limited by the VOA time response. Commercially available VOA's, such as the EXFO model 3100B-EA (EXFO Corporation, Quebec, Canada), can span a dynamic range (e.g., from 1.45 dB to 17 dB) in approximately 2.25 seconds or with a frequency response of 0.35 Hz. For applications using a BRD approach as set forth in the system of FIG. 4, the signal output from RM 90 in line 103 will become unsteady as some of the low-frequency signal associated with the change in reference-to-signal ratio passes through the 1 Hz high-pass filter. The dynamic range of the BRD output will be limited on one hand by the need to maintain a ref/sig ratio greater than unity and on the other hand by the upper bound of the detector's linear range. Therefore, dropouts in recorded data will occur during the time the control strategy is adjusting the VOA attenuation.

This problem is overcome by implementing a control strategy that consists of two main requirements. The first requirement is the need to define if the power irradiated on the BRD reference detector is critical. Here, the data is flagged for a validity check. Second, the required action of the VOA needs to be computed. A standard proportional integral derivative (PID) control algorithm can be used as a starting point, which can then be optimized based on measurement experience obtained from a given process. Outlined below are two main control modules, along with a initial list of variables associated with the control modules and having the following definitions:

Definitions:

"$P_{Probe}$" is defined as power falling on the BRD reference detector or auxiliary detector (e.g., photodetector 200 of the RM of FIG. 5) when the protective shutter is closed;

"$P_{Damage}$" is defined as the damage power threshold;

"$P_{MaxLin}$" is defined as the detector's upper power limit for linear performance;

"$P_{Min}$" is defined as the lower power limit before BRD goes unstable; and

"$P_{Target}$" is defined as detector power which yields a BRD ratio of 2.

First Control Module: Define Power State

When $P_{Probe} > P_{Damage}$, close the shutter.

When $P_{Probe} > P_{MaxLin}$, the detector is operating in a non-linear range and the data needs to be flagged.

When $P_{Probe} < P_{Min}$, the BRD ratio is inverted and the data needs to be flagged.

Second Control Module: Adjust VOA

The error between the power irradiating the detector and target power, or $e^j$, is defined as:

$$e^j = P_{Probe}{}^j - P_{Target} \tag{3}$$

where:

j is an index representative of an individual data acquisition point.

The attenuation setting is computed using the following algorithm:

$$A^{j+1} = A^j + \Delta A^j, \tag{4}$$

and $$\Delta A^j = k_c \left( e^j + \frac{1}{n} \sum_{k=(j-n)}^{j} e^k + T_d(e^j - e^{j-1}) \right) \tag{5}$$

where:

$k_c$ is the power output or gain;

n is the number of steps required for the integral response to equal the proportional response to a step input; and $T_d$ is a coefficient for the derivative term.

It is expected that the measured error signal will be noisy and the derivative aspect of the control algorithm may be inactivated by nulling $T_d$.

Laboratory experience with the commercially available VOA's, such as the EXFO VOA models, indicates that data obtained during a VOA adjustment is typically unusable. Thus, adjustments to the VOA are not made at a frequency defined by the j index (or data acquisition rate). Rather, the PID algorithm described above will be contained in a loop that acts as a filter, and discrete change adjustments to the VOA will be made at predefined intervals defined by N according to the following algorithm:

$$A^{i+1} = A^i + \frac{1}{N} \sum_{j=1}^{N} \Delta A^j \tag{6}$$

where:

N is equal to a preselected number of j intervals.

This algorithm will also serve as an opportunity to reset the summation term in the integral portion of the controller to reduce the effect of "wind up."

Control of the VOA is not limited to the use of a PID control strategy. Alternative approaches based on predictive control theory or neural networks can also be applied. The choice of the VOA control strategy used will be dependent on the process conditions, data available for model construction, required measurement time response, and acceptable level where process data is not collected.

As noted above, alternative attenuation devices that provide a faster time response (e.g., MEMS devices) can also be used. Thus, although the systems as described herein utilize a VOA for attenuation, it is noted that any device that can provide a selected level of controlled attenuation of light for the output signal from the FA can be implemented in accordance with the present invention. However, when utilizing a commercial VOA, a determination is required of the magnitude of the etalon contribution that will degrade the measurement performance. A custom VOA device based on the VOA technology of EXFO Corporation (Quebec, Canada) with a brushless motor is one possible alternative to provide a faster time-response compared to other off-the-shelf EXFO systems. Commercial VOA devices, such as the EXFO type, are designed to provide a precise attenuation, but with the cost of increased delay time. However, in the systems and methods of the present invention, VOA tolerance and precise attenuation adjustment are not critical. In addition, maintaining a ref/sig ratio of 2 is not a strict requirement of the present invention, and operating over a range of ratio values is acceptable.

Figure 6:
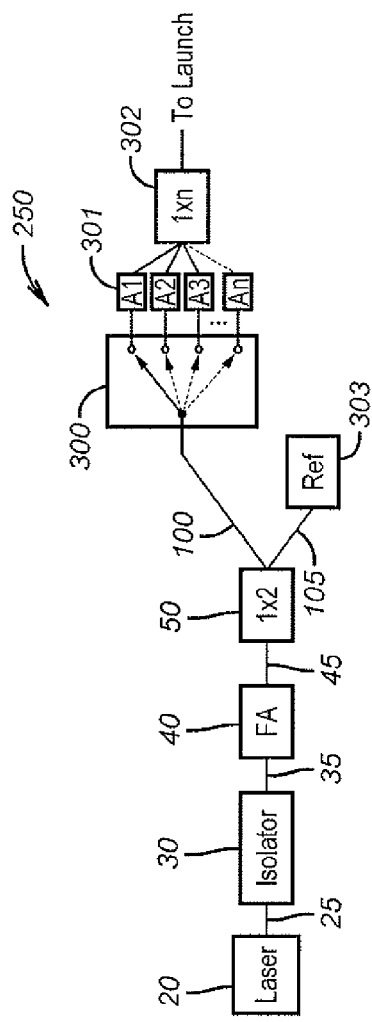
FIG. 6 depicts another embodiment of a gas species monitoring system utilizing a combination of a fiber amplifier (FA), an optical switch and a series of fixed optical attenuators in accordance with the present invention.
Figure 7:
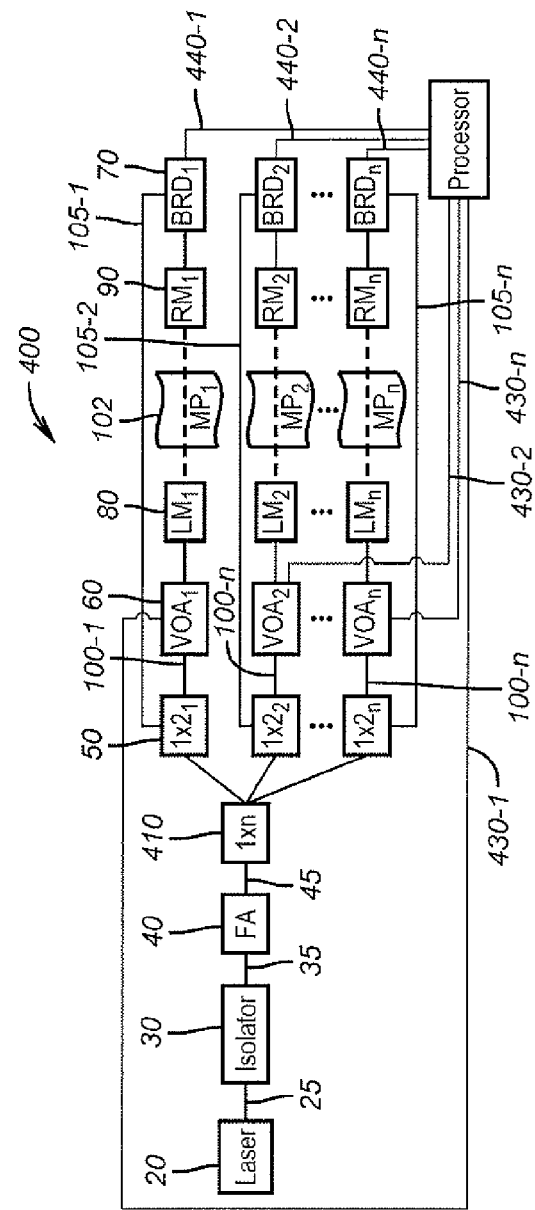
FIG. 7 depicts yet another embodiment of a gas species monitoring system utilizing a combination of a fiber amplifier (FA), a splitter and a series of variable optical attenuators (VOA's) to serve multiple measurement points (MP's) in accordance with the present invention.

Since precise control of the attenuation is not a strict requirement of the VOA, an alternative approach using a discrete VOA can be implemented by using an optical switch in the system, such as the system depicted in FIG. 6. Referring to FIG. 6, the system 250 includes a diode laser 20, isolator 30, FA 40 and 1×2 splitter 50 arranged in the same manner with respect to each other as for the system described above and depicted in FIG. 4. In addition, splitter 50 divides the laser beam or signal into two optical legs or lines 100 and 105 and at any selected power levels (e.g., about 70% to line 105 and about 30% to line 100). The input laser radiation is transported through line 100 to an optical switch 300 that includes any selected number (i.e., 1 to n) of channel configurations. An exemplary optical switch that is suitable for use in the present invention is the Prism Switch available in 1×4, 1×8, and 1×16 channel configurations from DiCon Fiberoptics, Inc. (Richmond, Calif.). A reference signal is also transported through line 105 to a reference system 303 (e.g., a BRD as described above for the system of FIG. 4).

A series of fixed optical attenuators $A_1, A_2, A_3, \ldots A_n$ (listed generally as 301 in FIG. 6) are separately and independently connected to the channel outputs of optical switch 300. The fixed optical attenuators can be of any suitable type including, without limitation the FA-300 series that are available in a range of 1 dB to 20 dB values from Oz Optics (Ontario, Canada). Thus, providing a set of fixed optical attenuators across 4, 8, or 16 channels as set forth in FIG. 6 will allow selection of the laser power required with the number of channels defining the resolution of the laser power selection.

A 1×n combiner 302 is separately connected, via a series of fiber optic lines, to each fixed optical attenuator $A_1, A_2, A_3, \ldots A_n$, to facilitate the delivery of radiation from a selected channel of the optical switch 300, and through a corresponding fixed optical attenuator in preparation for directing the laser signal to a measurement point (MP). Although not shown in FIG. 6, the system further includes a launch module (LM), a measurement point (MP) and receiver module (RM) configured and operable in a similar manner as described above for the system depicted in FIG. 4 (with the RM also connected to the reference system), such that the LM receives the attenuated signal from the combiner 302. With this configuration, the switching between the channels can be performed as fast as 10 msec, with a maximum switch time of 100 msec for a full 16-channel sweep. In addition, the system can also include a processor in communication with at least the reference system 303 and the optical switch 300 to facilitate selective and automated control of the switching of the optical switch (so as to divert the signal through a selected channel in the switch for attenuation to a selected degree by a corresponding fixed optical attenuator) based upon information received from the reference system and in a manner similar to the methods described above.

Alternative switch systems can also be used, such as a DiCon VX500 opto-mechanical device (DiCon Fiberoptics, Inc. of Richmond, Calif.) that uses a high-resolution stepper motor to switch between channels. However, the time response for this switch can be limiting. Thus, depending upon a particular application, the selection of an appropriate switch technology will depend upon the required time response and laser power resolution for the application. However, independent of the switch technology, the channel selection is based on the monitored laser intensity using either the signal detector in the RM when conditions are suitable as discussed previously or using the continuous laser power monitoring control strategy as described above and utilizing the RM configuration depicted in FIG. 5.

In another embodiment of the present invention, a system is provided that includes variable optical attenuation and multiplexing after fiber amplification to facilitate dividing the laser power output into multiple fiber optic lines for monitoring multiple measurement points (MP's). As a background, standard telecommunication DFB diode lasers typically provide 20-40 mW of power. For a multiplex application, the number of measurement points is limited due to the power limitation on the laser that would typically allow only 2 or 3 measurement points. However, this number is dependent on the transmission and background interferences that can degrade the measurement. To overcome this problem, multiplexed systems using optical switches have been proposed. However, multiplexing with optical switches does not allow simultaneous point monitoring. In addition, the signal averaging required for tunable diode absorption measurements typically range from 1-5 seconds or more for industrial process monitoring. Therefore, as the number of monitoring points increases, the measurement frequency at each location will decrease.

For example, a process or plant that requires 10 measurement locations with a sampling time of 2 seconds per location, i.e., 400 average spectra with the laser scan rate of 200 Hz, results in a sampling frequency of 0.05 Hz. However, by implementing a fiber amplifier within the system, the laser output can be amplified from 20 mW to 200 mW and distributed to the different locations with a 1×10 splitter providing 20 mW per location. Thus, the measurements can be performed simultaneously in the fiber amplifier system with a sampling frequency of 0.5 Hz for 2 seconds averaging time using a 200 Hz laser scan rate.

Further, improvement and control can be obtained, in accordance with the present invention, by the addition of a VOA for all or selected channels that require continuous control of the laser power. An exemplary embodiment of a gas species monitoring system 400 employing a laser with a FA/VOA combination in a multiplexed application is depicted in FIG. 7. A laser 20, isolator 30 and FA 40 are all connected via fiber optic lines in a similar manner as described above for the system depicted in FIG. 4. A 1×n splitter 410 receives an amplified signal from FA 40, via an fiber optic line 45, and splits the laser signal into a selected number (n) of separate and independent laser signals, where each laser signal can be at the same or different power levels with respect to other divided laser signals. Each split laser signal n is directed through a respective one of n channels or circuits, where each circuit includes a 1×2 splitter 50, a VOA 60, a LM 80, a MP 102, a RM 90 and a BRD 70 (with subscripts 1, 2, . . . n associated with each of the LM, MP, RM and BRD components as set forth in FIG. 7 to identify a respective one of the 1, 2, . . . and n circuits). While only three circuits are shown in FIG. 7, it is to be understood that any suitable number of circuits may be provided within system 400, depending upon the number of applications and measurement points (MP's) required for a particular application. Each circuit is further configured in the same manner as the system described above and depicted in FIG. 4, where a 1×2 splitter 50 for each circuit splits the signal into two legs or lines, with one line (designated as one of lines 100-1, 100-2, . . . 100-n) directing a split signal to a respective VOA 60 and the other line (designated as one of lines 105-1, 105-2, . . . 105-n) directing a split reference signal to a respective BRD 70 of the circuit.

A processor 420 is separately and independently connected to the BRD 70 and VOA 60 of each circuit, via suitable communication links 430-1 to 430-n and 440-1 to 440-n (e.g., electrical wiring and/or wireless communication links), and in a manner similar to that described above for the system depicted in FIG. 4, so as to facilitate selective and independent control of each VOA 60 during system operation. Thus, each circuit can be selectively and independently controlled based on the laser power level monitored after passing through the respective MP 102. In addition, the RM 90 of each system may further include the multiple photodetector arrangement as described above and depicted in FIG. 5. Feedback control of each VOA 60 is determined either by the direct laser power monitoring method or the control strategy as described above. Thus, the system 400 of FIG. 7 facilitates simultaneous gas species monitoring of multiple measurement points (MP's).

Figure 8:
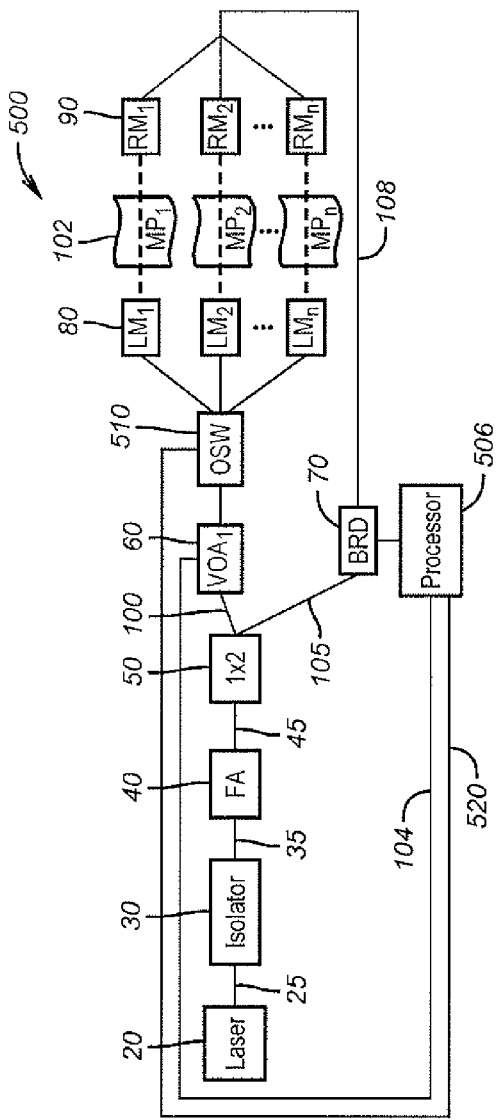
FIG. 8 depicts a further embodiment of a gas species monitoring system utilizing a combination of a fiber amplifier (FA), a variable optical attenuator (VOA) and a splitter to serve multiple measurement points (MP's) in accordance with the present invention.

In a further embodiment of the present invention, a combination of a fiber amplifier, VOA, and optical switch (FA/VOA/OS) are used for multiple point measurements. An exemplary system 500 employing this combination of components is depicted in FIG. 8. System 500 includes a laser 20, isolator 30, FA 40, and 1×2 splitter 50 all connected with each other, via fiber optic lines, in a manner similar to that described above for the system of FIG. 4. In addition, the 1×2 splitter 50 divides the laser signal into two legs or lines 100 and 105 to send the split signals to a VOA 60 and a BRD in a manner similar to that described above for the system of FIG. 4. The VOA 60 delivers the attenuated signal, via an fiber optic line, to a 1×n optical switch 510. The optical switch 510 is separately and independently connected, via fiber optic lines, to a series of n circuits. Each circuit includes a LM 80, a MP 102 and a RM 90 (with subscripts 1, 2, ... n associated with each of the LM, MP and RM components as set forth in FIG. 8 to identify a respective one of the 1, 2, ... and n circuits). While only three circuits are shown in FIG. 8, it is to be understood that any suitable number of circuits may be provided within system 500, depending upon the number of applications and measurement points (MP's) required for a particular application. Each RM 90 is further connected, via a main fiber optic line 108, to BRD 70 to provide the detected signal to the BRD for analysis. A processor 506 is also connected, via respective communication links 104, 107 and 520 (e.g., electrical wiring and/or wireless links), to VOA 60, BRD 70 and optical switch 510.

In system 500, control of the laser power delivered to each measurement point (MP) 90 is based on the measured transmission through the process. The channel selection to a MP 90 is selected by manipulation of optical switch 510 by processor 506, and VOA 60 is then selectively adjusted by processor 506 to in turn adjust the laser power in order to optimize the measurement at the selected MP location. For applications where the transmission losses are known and relatively constant at one or more measurement points (MP's), the VOA's associated with each of these MP's can be replaced with fixed optical attenuators. However, as noted above, the use of an optical switch can increase the time required to acquire data at all monitoring locations. For dynamic processes, the measurement frequency at the location may not be adequate to capture the dynamics and aliasing in the data could be observed.

The different embodiments demonstrate the added flexibility obtained using a fiber amplifier with various combinations of a VOA and/or an optical switch. Selection of a specific combination, such as those described above and depicted in the figures, is dictated by the particular monitoring application. To illustrate this point, the following exemplary industrial applications are described employing the different system configurations of the present invention as described above and depicted in FIGS. 4-8.

The first industrial monitoring example is a single point monitoring location on an EAF (electric arc furnace) using the FA/VOA combination as described above and depicted in FIG. 4. The benefits of monitoring the off-gas composition from the EAF for post-combustion control are well known and commercial systems based on extractive sampling are commercially available. These systems monitor the composition of the extracted gas after conditioning, removal of water and particulate matter, with standard NDIR analyzers for CO and $CO_2$, paramagnetic resonance for $O_2$, and thermal conductivity for $H_2$ monitoring. The extractive sampling system for the off-gas sampling on the EAF is performed near the furnace exhaust gap (often referred to as the fourth hole). At this location, the particle density in the gas stream can be several 100 $g/m^3$ with temperatures near 1600° C. These harsh conditions are problematic to the sampling system and require frequent maintenance, since the gas sampled also contains the particle matter. In addition, the EAF operation is very dynamic with gas composition changes occurring on a short time scale. The slow response time of the extractive sampling due to both the sampling line lengths used and the inherent delays in the analyzers reduces the post combustion efficiency resulting in overshooting or under shooting the $O_2$ injection.

The off-gas monitoring problems encountered with extractive sampling are addressed as follows. Diode laser gas monitoring systems can provide a fast-time response measurement for monitoring CO concentration variations on a pilot furnace using an oscillating combustion technology. See W. Von Drasek, K. Mulderink, S. Wehe, and M. Allen *Multiple Gas Species Detection using a Tunable Diode Laser Sensor for Combustion Process Monitoring American Institute of Chemical Engineers* 2002 *Annual Meeting, Sensors for Process Control and for the Chemical Industry I*, Indianapolis, Ind., Nov. 3-8 2002; and Charon, O., Jouvaud, D., and Genies, B., "*Pulsed $O_2$/Fuel Flame as a New Technique for Low NOx Emissions*", *Comb. Sci. and Tech.*, Vol. 90, pp. 1-12, 1993. In addition, the laser measurement is performed in-situ with no gas sampling or conditioning required. However, the laser measurement is path-averaged and measurements in high particle density streams can degrade the results due to poor laser beam transmission.

Figure 9:
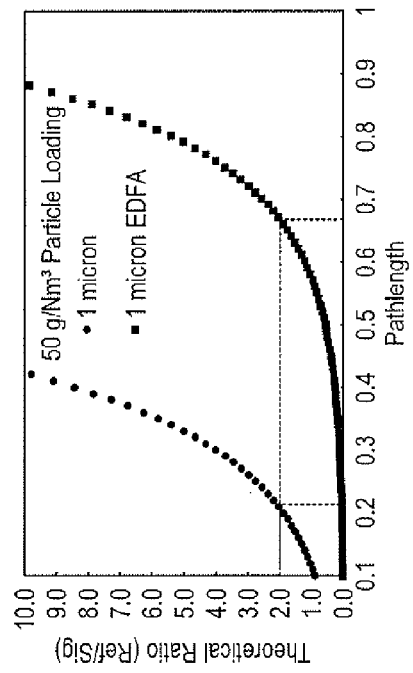
FIG. 9 is a plot of theoretical ref/sig ratio vs. pathlength for diode laser gas monitoring of a high particle density stream having a loading density of 50 g/Nm$^3$ and particle sizes of 1 micron.

To illustrate the effect of poor laser beam transmission in conventional diode laser gas monitoring systems, calculation results of theoretical ref/sig ratio values vs. pathlength are ploted in FIG. 9 for laser gas monitoring of a high particle density stream having a loading density of 50 $g/Nm^3$ and particle sizes of 1 micron (i.e., the plot identified as "1 micron"). For this example, the diode laser gas monitoring system is based on BRD technology where the dynamic response of the photocurrent cancellation circuit occurs at ref/sig ratio near 2. Note, the use of the BRD near 2 is not a strict requirement and ratios >2 can be used. However, as this ratio increases, the laser radiation power reaching the detector is decreasing and background radiation, e.g., from black body particle emission, will dominate and degrade the measurement.

Using standard telecommunication diode lasers with no amplification the monitoring pathlength is limited to about 0.19 m to achieve the desired ref/sig ratio. When implementing an amplifier that delivers 177 mW to the process, with 2.48 mW fixed for the ref channel, a monitoring pathlength of 0.66 m can be used. The ability to perform the measurement at longer pathlengths has two important consequences. First, the absorption measurement is pathlength dependent with measured signal, i.e., the integrated area under the absorption feature, is proportional to the pathlength. Therefore, signal-to-noise ration (SNR) improvements of the same order as the pathlength change are experienced. For example, a factor of 3 improvement for SNR is realized in this example. Second, the installation requirements are relaxed by not requiring long beam shielding tubes to control the measurement pathlength, as described in U.S. Patent Application Publication No. 2003/0218752 and also Dietrich, A., Kaspersen, P., and Sommerauer, H., "*Laser Analysis of CO and Oxygen in EAF Off-Gas*", 59th *Electric Furnace Conference and* 19th *Process Technology Conference Proceedings, Iron and Steel Society*, 2001.

Utilizing the system described above and depicted in FIG. 4 for EAF monitoring, the amplifier can operate in the gain saturated mode with the laser power delivered to the process controlled by the VOA. The process dynamics dictate the level of laser power required to maintain a ref/sig ratio near 2. However, if the process transmission characteristic varies rapidly, resulting in the laser power exceeding the threshold value, then the safety shutter previously described and shown in the RM configuration of FIG. 5 will isolate the detector from damage. In this application, CO and $H_2O$ monitoring can be performed with a single diode laser such as the type described in U.S. Patent Application Publication No. 2003/0132389. Monitoring the CO concentration can then be used for post-combustion control by $O_2$ injection based on the level of CO observed. Gas temperature is monitored from the multiple lines of $H_2O$ observed near 1560 nm in a similar manner as described in U.S. Patent Application Publication No. 2003/0132389. In addition, $H_2O$ monitoring can be used for leak detection of the water-cooling system of the furnace. This can be performed once the statistical range of $H_2O$ concentration from several heats is established. Measurements showing consistently higher than normal values can then be attributed to potential water-cooling leaks from the process. Finally, the combination of gas species concentration and temperature can be used for real-time mass and energy balances by including the additional process information such as fuel flow rate, $O_2$ flow rate, electrical power, etc.

In another industrial application example, a system employing the combination of FA/VOA with multiple measurement points (MP's), as described above and as depicted in FIGS. 7 and 8, can be used for plant wide monitoring requirements.

In this example a steel mill is used to illustrate the MP measurements, where a central unit housing the laser and associated electronics is located in a plant control room from which distributes the laser power to multiple points in the plant. In steel making the raw material (scrap or ore) is processed to the desired chemistry and temperature for forming into billets or slabs. In the melting process, an EAF is used for scrap melting as previously discussed or a blast furnace is used for raw ore processing. For both of these processes, the operating conditions are harsh (i.e., high temperature with high particle densities), requiring special considerations for conducting the measurement such as reduction of the pathlength and/or increasing the laser power. For laser power boost and control, the combination of FA/VOA is utilized in the manner described above.

In addition, other plant MP's can be implemented by using a fiber splitter to transport the beam to various MP's of interest including, without limitation, CO/$H_2O$ monitoring in heat treating furnaces, ambient CO monitoring around the EAF process, CO monitoring in the EAF exhaust duct before the bag house for explosion prevention, and CO/$H_2O$ monitoring in different zones of the reheat furnace. With this approach, a single laser control/data acquisition processor is used for monitoring at different locations and under different conditions requiring control of the laser power.

Other examples for implementing any of the previously described systems of the present invention include systems with aluminum rotary furnace monitoring for control of CO to reduce the dross level. In these processes, the transmission level varies in time due to the variation in particulate loading in the exhaust stream. Furthermore, plants generally have several rotary furnaces on-site and operating independently from each other, with each furnace requiring some mechanism for monitoring the CO within the system. With the FA/VOA combination, the amplified radiation can be transported to a 1×n splitter followed by a VOA before the launching the beam, via the LM, across the process. The overall system configuration could, for example, follow the layout described in FIG. 7, with a VOA for each individual rotary furnace to provide independent laser power control based on feedback from the process of the transmission level. Maintaining the optimum laser power for each process will ensure the measurement quality is maintained throughout the melting cycle to avoid measurement drop-outs (e.g., if transmission becomes too weak for measurement) during high particle loading times and avoid electronic saturation during low particle loading when laser beam transmission is high.

The present invention is not limited to the embodiments described above, but can include any suitable combination of a FA with a variable optical attenuation system. For example, several FA/VOA combinations can be used in series and as needed for a particular scenario. Furthermore, placement of a FA/VOA combination is not limited to requiring a 1×2 splitter to follow such combination. Rather, a 1×n splitter could following the FA/VOA combination, where n is any selected number of 3 or greater. In addition, the laser power can be split between a plurality of legs or lines, where only one or less than the total number of the split legs require the need for dynamic laser power control.

In another embodiment, improved dynamic range of the measurement is obtained by operating the FA in the saturation mode. Operating in this mode almost completely nulls the variation of the laser power as the wavelength of the laser is swept by varying the current injection. For gas species monitoring, acquiring the full absorption feature that includes a portion of the baseline to the left and right of the absorption peak is the preferred mode of operation. By obtaining a portion of the baseline, the absorption feature relative to the baseline is measured even when broadband emitters or absorbers are present. However, tuning the diode by current injection not only varies the wavelength but also the laser output power. For a 1 cm$^{-1}$ tuning range the laser power can vary by 30-40%. In cases where the measurement is amplified for small signal detection, the range of gain is limited due to the power variation in the laser. As the gain is increased, saturation of the electronics will occur first in the high laser power region thereby setting the limit on the acceptable gain level.

Figure 10:
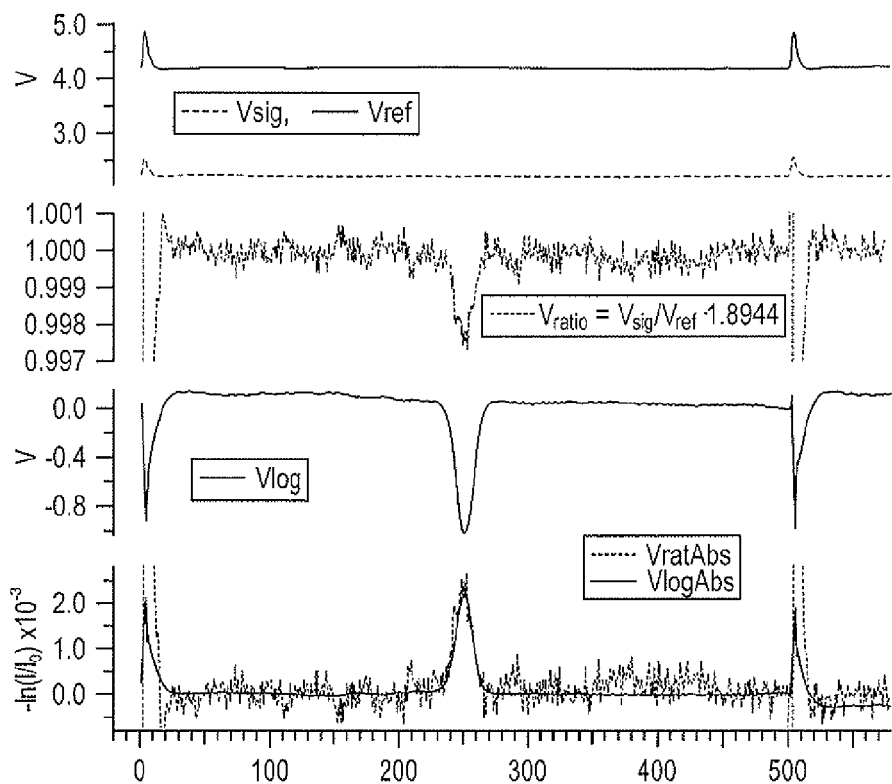
FIG. 10 is a plot showing the linear channel outputs Vsig and Vref data as well as measured BRD absorbance values obtained by a process CO monitoring in a 50 cm cell and utilizing a system setup similar to the system of FIG. 4.
Figure 10:
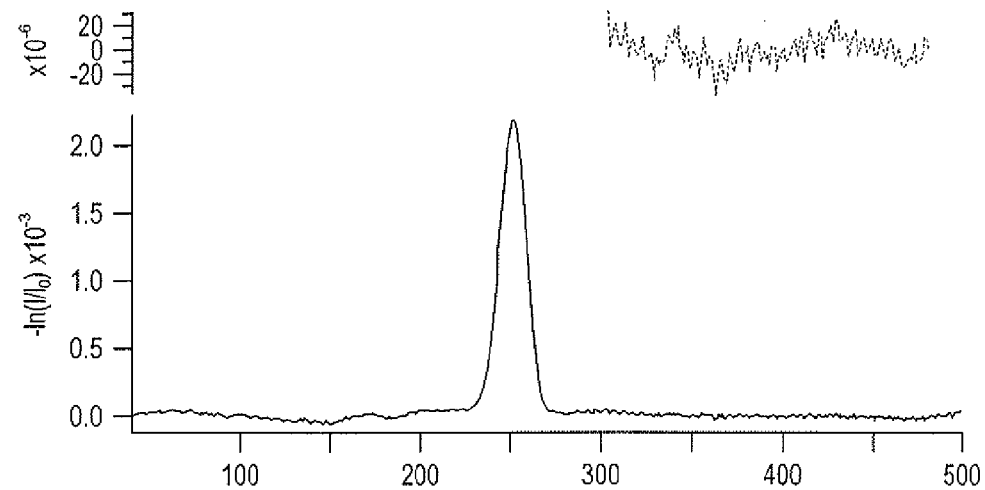

However, with the FA operating in saturation mode, the variation in laser power over the wavelength tuning range is nearly flat, as shown in FIG. 10 for CO monitoring of the R(14) line at ambient conditions in a 50 cm cell. In particular, these measurements were obtained using a system configuration similar to the system described above and depicted in FIG. 4. The output of the EDFA for this experiment was 23.7 dBm (234 mW). The average input power to the EDFA was approximately 7 mW. The attenuation of the VOA was set to 17.005 dB (with a built-in 0.005 dB offset). The first two traces of plotted data at the top portion of FIG. 10 show the linear channel outputs Vref and Vsig. The only variations from the baseline in the Vref and Vsig signals occur at the beginning and end of the scan. This anomaly is attributed to the internal operation of the amplifier near these transition regions. Nevertheless, the constant laser power over the laser-tuning window allows selection of higher gain values that would otherwise be unacceptable due to electronic saturation.

The next trace of plotted data in FIG. 10 directly below the Vref and Vsig data depicts the ratio of the ref and sig channels to show the resulting raw transmission measurement indicated as Vratio. Directly below the Vratio trace, the resulting Vlog signal from the BRD is displayed, which shows the improved signal-to-noise ratio (SNR) obtained. The plot directly below the Vlog trace shows two calculations of the absorbance, with one trace being calculated from the inverted-baseline-corrected Vlog signal (VlogAbs) and the other trace being calculated from the normalized transmission (VratAbs). In addition, the bottom plots show the absorbance spectrum from the Vlog signal along with the noise equivalent absorbance taken as a SNR of 1 in the wings of the absorption lineshape with a RMS value of $1.1 \times 10^{-5}$ in the wing of the spectrum.

In addition to the improved dynamic range through higher gain amplification, the nearly constant laser power produces a baseline that is close to being linear. The nearly linear baseline improves the measurement accuracy by reducing the order of the polynomial used in performing the baseline correction. The standard method for measuring an absorption signal relative to the baseline requires selecting a portion of the spectra before and after the absorption feature. Ideally, the portion selected has no absorption features present. An nth order polynomial is fitted through the two selected regions that are then used to correct the full measured spectrum by subtracting the fitted baseline from the spectrum. The degree of curvature in the measured spectrum dictates the order of the polynomial required for the baseline correction. The uncertainty in the correction occurs in the region where the absorption feature of interest lies. In this region, the measured data is not used in determining the baseline correction and erroneous curvature through this region will contribute to the measurement error. Using the FA, a nearly flat baseline is obtained, as shown in FIG. 9 (i.e., the plot identified as "1 micron EDFA"). In this case, the order of the polynomial can be reduced, thereby removing uncertainty in the baseline correction resulting in improved measurement accuracy.

Another aspect of the present invention involves the use of a polarization maintaining EDFA (PM-EDFA, e.g., Keopsys Inc., Piftstown, N. J., model OEM-C-30-BO-PM) with polarization maintaining (PM) fiber optic cables for transporting the amplified laser light to the launch module. This combination is advantageous when polarization sensitive optical components such as, mirrors, gratings, prisms, and optical detectors, are used in the sensor system. For industrial applications where the fiber optic cables transporting the laser light from the amplifier to the process experience mechanical vibration or stresses and/or large temperature effects large variations in the monitored laser intensity can occur. The intensity variations observed when using polarization sensitive optic components are attributed to the use of single-mode fibers that carry two modes, i.e., vertical, and horizontal, with orthogonal polarization. For a perfect wave guide, the two modes are degenerate so that light can shift between the two polarization modes. Thus, if the fibers were perfectly circular the polarization would have little effect. However, real fibers are not axially symmetric, perfectly straight, nor completely isotropic. The imperfection in the fiber leads to a complete mixing of the two polarization modes, such that initially launched linearly polarized light quickly reaches a state of arbitrary polarization. Furthermore, environmental perturbations on the fiber, e.g., twists, bends, anisotropic stresses, surrounding temperature conditions, etc., results in unstable fluctuations of the polarization mode. Using the PM EDFA and PM fiber combination will minimize the polarization effects on the measurement when polarization sensitive components are used.

Still another aspect of the invention is the use of depolarizers with a standard EDFA system. This configuration utilizes a passive fiber optic depolarizer based on spectral averaging using a crystal depolarizer of the Lyot type as supplied by Phoenix Photonics Limited (Wallington, United Kingdom). Alternatively a polarization scrambler, e.g., the PolaMIX™ from General Photonics Corp. (Chino, Calif.), can be used. These devices are not purely passive since an external power supply is required. Here the advantage is less wavelength dependence as compared to the Lyot type which is highly dependent on the coherent length of the laser output. In either case, insertion of a depolarizing device after the EDFA will produce pseudo-random polarization output, i.e., the degree of polarization is reduced to less than 5% in general or as low as 0.24% based on the Phoenix Photonics device DPOL-1. Suppression of the polarization for the launched light into the standard single mode fiber removes the sensitivity to fiber imperfections and outside environmental effects such as, mechanical vibrations, stresses, and temperature variation, that will enhance the measurement quality when polarization sensitive components are used in the detection scheme.

Thus, the combination of a FA with a variable optical attenuation system as in the systems described above for use in a gas species monitoring system renders the system operable in both a dynamic or steady state mode. In addition, using such a combination with beam splitters and/or optical switches extends the range of multiplexed measurement applications that can be implemented utilizing this system. With this configuration, a plant-wide distributed measurement system can be performed using a single diode laser that is adaptable to measurement points with varying process conditions, e.g., transmission characteristics.

Figure 11:
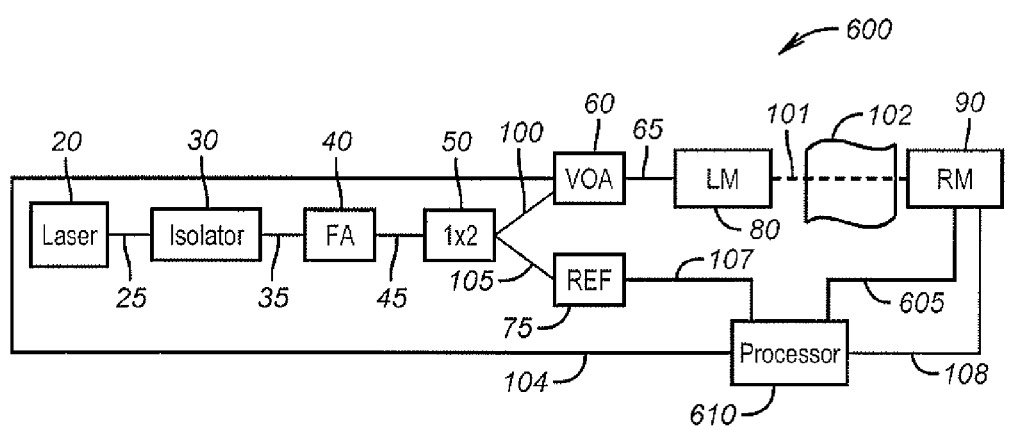
FIG. 11 depicts still another embodiment of a gas species monitoring system utilizing a combination of a fiber amplifier (FA) and variable optical aftenuator (VOA), along with a reference system in accordance with the present invention.

As noted above, while the exemplary embodiments described herein utilized BRD technology, the present invention is not limited to such technology. In particular, the BRD can be replaced with a general reference system 72, as depicted in FIG. 11, including a reference cell from a wavelength modulated or frequency modulated system or direct absorption system. The reference cell can be used for laser line locking and, if desired, as a calibration source. The preferred mode of operation is with the FA placed before the reference and measurement channels, since the FA will flatten the baseline variation as the laser wavelength is swept. Tracking the same variations in the measurement and reference channels improves the overall measurement quality with reduced post-processing requirements.

Referring to FIG. 11, system 600 includes a laser 20, isolator 30, FA 40, 1×2 splitter 60, VOA 60, LM 80, MP 102 and RM 90 all arranged with respect to each other in a similar manner as the system described above and depicted in FIG. 4. System 600 further includes a reference system 75 that receives a split signal from line 105 of the splitter 50. A processor 610 is in communication with the VOA 60 (via communication link 104), the reference system 75 (via communication link 107) and the RM 90 (via communication link 605). The processor further receives information from the reference system 75 regarding the reference signal and information from the RM 90 regarding a processed signal from the photodetector in the RM, and further controls the VOA 60 based upon a comparison of these signals as well as in accordance with any of the previously described methods.

In addition, as noted above, the invention is not limited to the use of a reference system (e.g., a BRD) to facilitate selective adjustment of the VOA. The system can be configured such that the processor receives measured signal information directly from the photodetector of the RM, and the VOA is then adjusted accordingly based upon the signal level as measured by the RM detector (e.g., the VOA can be adjusted in a suitable manner so as to prevent saturation from occurring at the detection electronics within the RM). In particular, for direct absorption systems not using a reference channel, i.e., measurements that are made relative to the transmitted baseline, all of the embodiments and additional concepts as described above can also be carried out without the use of a 1×2 splitter to split the amplified signal and/or the reference system to generate a reference signal.

Having described novel systems and methods for dynamic laser power control for gas species monitoring, it is believed that other modifications, variations and changes will be suggested to those skilled in the art in view of the teachings set forth herein. It is therefore to be understood that all such variations, modifications and changes are believed to fall within the scope of the present invention as defined by the appended claims.

The invention claimed is:

1. A gas species monitoring system comprising:
a laser;
a fiber amplifier configured to receive an input signal from the laser and generate an amplified signal;
a variable optical attenuation system configured to receive at least a portion of the amplified signal and generate an attenuated signal for delivery to a measurement point, the measurement point including a gaseous fluid;
a detector configured to receive and process a signal from the measurement point so as to obtain a measured signal that correlates with the presence of a gas species within the gaseous fluid at the measurement point; and
a processor in communication with at least the variable optical attenuation system and the detector and configured to control the variable optical attenuation system based upon the measured signal.

2. A gas species monitoring system comprising:
a laser;
a fiber amplifier configured to receive an input signal from the laser and generate an amplified signal at a greater power level than the input signal;
a variable optical attenuation system configured to receive and process the amplified signal so as to obtain an attenuated signal at a selected power level;
a gas species detection zone including at least one circuit comprising:
a launch module configured to receive the attenuated signal from the variable optical attenuation system and collimate the signal for delivery to a measurement point, the measurement point including a gaseous fluid; and
a receiver module configured to receive the signal emerging from the measurement point, the receiver module including a detector configured to process the signal from the measurement point so as to obtain a measured signal that correlates with the presence of at least one gas species within the gaseous fluid; and
a processor in communication with at least the detector of the receiver module and the variable optical attenuation system, wherein the processor receives information regarding the measured signal and selectively controls the variable optical attenuation system based upon at least the measured signal.

3. The gas species monitoring system of claim 2, wherein the receiver module further comprises:
a second detector;
a wedge optic configured to divert a portion of the signal received from the measurement point to the second detector; and
an adjustable shutter configured to control the propagation of the signal received from the measurement point to the detector;
wherein the adjustable shutter remains open when the power of the diverted portion of the signal received by the second detector is less than a set-point value, and the shutter is to selectively manipulated to a closed position to prevent the signal received from the measurement point from reaching the detector when the power of the diverted portion of the signal received by the second detector is equal or greater than the set-point value.

4. The gas species monitoring system of claim 2, further comprising:
a splitter device configured to split the amplified signal into a plurality of split signals, with at least one split signal being sent to the variable optical attenuation system; and
a reference system configured to receive and process a split signal from the splitter device so as to obtain a reference signal;
wherein the processor is further in communication with the reference system and receives information regarding the reference signal and selectively controls the variable optical attenuation system based upon a comparison of the measured signal with the reference signal.

5. The gas species monitoring system of claim 4, wherein the reference system comprises a balance ratiometric detector, and the balance ratiometric detector is further configured to receive the measured signal from the receiver module.

6. The gas species monitoring system of claim 2, wherein the variable optical attenuation system comprises a selectively adjustable variable optical attenuator.

7. The gas species monitoring system of claim 2, wherein the variable optical attenuation system comprises:
an optical switch including a plurality of optical channels;
a plurality of fixed attenuators, each attenuator connected to a respective optical channel of the optical switch and configured to attenuate a signal received from the optical switch to a selected power level; and
a combiner including a plurality of optical channels, the combiner being separately and independently connected to an output of each fixed attenuator via a respective optical channel of the combiner;
wherein the optical splitter is selectively adjustable to divert the amplified signal through a selected fixed optical attenuator prior to being sent to the combiner.

8. The gas species monitoring system of claim 2, further comprising a splitter device configured to split the amplified signal into a plurality of split signals, wherein the gas species detection zone includes a plurality of circuits, each circuit being configured to receive a split and attenuated signal so as to facilitate selective measurements of gas species at a plurality of measurement points.

9. The gas species monitoring system of claim 8, wherein:
the variable optical attenuation system comprises a plurality of independently adjustable variable optical attenuators, each variable optical attenuator being configured to attenuate a split signal received from the splitter device and connected with a respective circuit of the gas species detection zone to facilitate delivery of the attenuated signal to a launch module of the respective circuit;

wherein the processor receives information from a detector of the receiver module of each circuit regarding the measured signal of the respective circuit and selectively and independently controls the variable optical attenuator connected with each circuit based upon the measured signal of the respective circuit.

10. The gas species monitoring system of claim 8, wherein the variable optical attenuator system comprises a selectively adjustable variable optical attenuator, and the gas species monitoring system further comprises:

an optical switch device configured to receive the attenuated signal from the variable optical attenuator and including a plurality of optical channels, each optical channel conesponding with a respective circuit of the gas species detection zone to facilitate selective transfer of the attenuated signal through a selected optical channel and respective circuit;

wherein the processor is further in communication with the optical switch device to selectively control the optical switch device and the direction of the attenuated signal through a selected circuit and to a selected measurement point.

11. The gas species monitoring system of claim 2, wherein the fiber amplifier comprises a polarization maintaining erbium doped fiber amplifier, and wherein the system further includes polarization maintaining (PM) fiber optic cables for transporting amplified and attenuated signals to the launch module.

12. The gas species monitoring system of claim 2, wherein the fiber amplifier comprises an erbium doped fiber amplifier, and wherein the system further includes a depolarizer configured to receive the amplified signal from the erbium doped fiber amplifier and reduce the degree of polarization of the signal prior to delivery to the launch module.

* * * * *

UNITED STATES PATENT AND TRADEMARK OFFICE
CERTIFICATE OF CORRECTION

PATENT NO.       : 7,409,117 B2
APPLICATION NO.  : 11/045513
DATED            : August 5, 2008
INVENTOR(S)      : William A. Von Drasek et al.

It is certified that error appears in the above-identified patent and that said Letters Patent is hereby corrected as shown below:

Delete the text from column 22, line 34 through and including column 24, line 5.

Signed and Sealed this

Twentieth Day of April, 2010

David J. Kappos
*Director of the United States Patent and Trademark Office*